United States Patent [19]

Broekhof et al.

[11] Patent Number: 5,162,551
[45] Date of Patent: Nov. 10, 1992

[54] PROCESS FOR THE PREPARATION OF DIHYDROPYRANS

[75] Inventors: Nicolaas L. Broekhof, Naarden; Jogchum J. Hofma, Amersfoort, both of Netherlands

[73] Assignee: Naarden International, N.V., Naarden, Netherlands

[21] Appl. No.: 293,519

[22] Filed: Jan. 5, 1989

[30] Foreign Application Priority Data

Jan. 5, 1988 [NL] Netherlands ............... 8800009

[51] Int. Cl.$^5$ .................................. C07D 309/18
[52] U.S. Cl. .............................. 549/356; 549/381
[58] Field of Search ........................ 549/356, 381

[56] References Cited

U.S. PATENT DOCUMENTS 4,163,758  8/1979  Kondo et al. .................. 549/421
4,837,344  6/1989  Miyaji et al. .................. 549/319

FOREIGN PATENT DOCUMENTS 0013822  10/1971  Australia .
883039  11/1981  U.S.S.R. .

OTHER PUBLICATIONS

Ansell et al, J. Chem. Soc., Chem. Comm., pp. 739–740 1972.
Falbe et al., Rompp Chemie Lexikon, pp. 956–957.
Organic Reactions, vol. 32, pp. 8–9, 1984.
Journal of Organic Chemistry, vol. 48, 1983, blz 3003–3010 Am. Chemical Society, Washington US Snider et al.
Monatshefte fur Chemie, vol. 107, 1976, blz 675–684—Springerverlag, DE; H. Griengl et al "Prins-Reaktionen mit Arylaldehyden".

*Primary Examiner*—C. Warren Ivy
*Assistant Examiner*—Ba K. Trinh
*Attorney, Agent, or Firm*—Cushman, Darby & Cushman

[57] ABSTRACT

The invention provides a process for the preparation of 5,6-dihydro-2H-pyran derivatives, wherein an aldehyde of formula I:

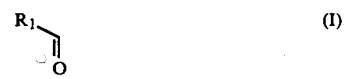

wherein $R_1$ represents an alkyl, cycloalkyl, aralkyl, alkaryl or aryl group having at most 15 carbon atoms and a diene of formula II:

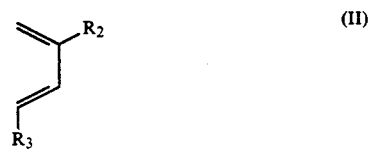

wherein $R_2$ and $R_3$ represents a hydrogen atom or an alkyl group having 1–6 carbon atoms are reacted in a Diels-Alder-type reaction under the influence of an inorganic Lewis acid catalyst, producing a compound of formula III wherein $R_1$–$R_3$ have the meaning given above.

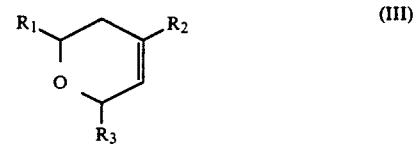

Preferably $R_1$ represents a 1–6 carbon atom alkyl group, a phenyl group or an o-, m- or p-tolyl group. Isoprene or 2-methyl-1,3-pentadiene is preferably used as the diene. The preferred catalyst is AlCl$_3$ or SnCl$_4$ and an organic nitro compound may be used as the co-catalyst.

4 Claims, No Drawings

PROCESS FOR THE PREPARATION OF DIHYDROPYRANS

The invention relates to a new process for the preparation of dihydropyrans. More particularly, the invention relates to a process for the preparation of substituted 5,6-dihydro-2H-pyrans.

Substituted dihydropyrans are important industrial raw materials. α-Phenyl-dihydropyrans can be converted by reductive ring opening in acidic medium, as described in M. Freifelder, Practical Catalytic Hydrogenation, Wiley-Interscience, New York (1971), page 412, into 5phenylpentanols, which can be of importance inter alia as perfumes. On the other hand, some dihydropyrans, such as 6-phenyl-4-methyl-5,6-dihydro-2H-pyran, 6-phenyl-2,4-dimethyl-5,6-dihydro-2H-pyran and 6-butyl-2,4-dimethyl-5,6-dihydro-2H-pyran are themselves also valuable perfumes, see e.g. U.S. Pat. No. 3,681,263 and A. A. Gevorkyan et al., Arm. Khim. Zh. 1976 29(3), pages 276-7, Chem. Abstr. 85 (1976), 10848e.

As described in the above-mentioned literature and in Swiss patent nr. 655,932, these and similar 5,6-dihydro-2H-pyrans are usually prepared by reaction of an aldehyde such as benzaldehyde or pentanal with a 3-butenol-1 substituted in the desired manner, such as isoprenol, under the influence of a catalytic amount of acid, resulting in a mixture of double bond isomers. The desired 3-butenols, however, are expensive or not commercially available at all. Therefore, there is a need for a method of preparing these dihydropyrans starting from readily available and inexpensive raw materials.

In theory such compounds could be synthesized by a Diels-Alder-type reaction between aldehydes functioning as dienophiles and dienes substituted in the desired manner. Dienes of this kind, such as isoprene and 2-methylpentadiene, are available on a large scale.

Studying the literature, however, forces one to the conclusion that Diels-Alder reactions between simple aliphatic or aromatic aldehydes and simple dienes are not possible, or only under extreme reaction conditions or with exotic and thus expensive catalysts; see e.g. S. M. Weinreb et al., Tetrahydron 1982, pages 3100-3104 and B. B. Snider et al., J. Org. Chem. 48 (1983), pages 3003-3010.

Surprisingly, it has now been found that 5,6-dihydro-2H-pyrans according to formula III:

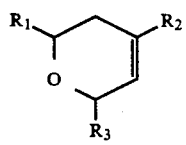

III wherein $R_1$ is an alkyl, cycloalkyl, aralkyl, alkaryl or aryl group having a maximum of 15 carbon atoms, and $R_2$ and $R_3$ represent a hydrogen atom or an alkyl group having 1-6 carbon atoms, can be prepared in a simple manner by a Diels-Alder reaction between an aldehyde according to formula I:

I and a diene according to formula II:

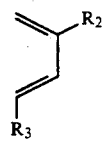

II in which formulae $R_1$, $R_2$ and $R_3$ have the meaning given above, under the influence of an inorganic Lewis acid as the catalyst.

$R_1$ is preferably an alkyl, aralkyl, alkaryl or aryl group having a maximum of 12 carbon atoms. Particularly suitable are straight or branched alkyl groups, the phenyl group and the ortho-, meta- and para-tolyl group. Isoprene and 2-methyl-1,3-pentadiene are particularly suitable as dienes.

Although the reaction can, in principle, be carried out with equimolar amounts of dienes and dienophiles, or even with an excess of dienophile, is has proved that it is preferable to use an excess of diene. A molar ratio of dienes/dienophiles between 1:1 and 10:1 is very suitable. Particularly suitable is a molar ratio between 1.5:1 and 2.5:1.

The reaction according to the invention is carried out under the influence of an inorganic Lewis acid catalyst, preferably $AlCl_3$ or $SnCl_4$. Particularly suitable is $AlCl_3$. The catalyst is used in an amount of at least 0.01 mol and preferably between 0.03 and 0.6 mol per mol of dienophile. As co-catalyst, an aliphatic or aromatic nitro compound can be added advantageously in an amount of a maximum of 10 mol per mol of catalyst. Preferably, amounts of 3 mol or less per mol of catalyst are used. Especially suitable for this purpose are: nitromethane, nitroethane, nitropropane and higher nitroalkanes, nitrobenzene and nitrocyclohexane.

The usual solvents for catalysed Diels-Alder reactions, particularly hydrocarbons, are suitable for the reaction to be carried out in. Examples of such solvents are benzene, toluene, xylene, pentane, hexane, cyclohexane, petroleum-ether and the like. These solvents are preferably used in an amount of at least 50 mol % (with respect to dienophile), particularly in an amount of 150 mol % or more.

The most suitable reaction temperature is dependent on the reactivity of the diene and dienophile, the catalyst and co-catalyst used and the amount thereof, as well as on the properties of the solvent. Generally, temperatures between −30° C. and +100° C. can be used. Especially suitable are temperatures between −20° C. and +70° C. When a co-catalyst is used, generally a sufficiently high reaction rate is already obtained at a temperature below about 30° C. When an aliphatic or alicyclic hydrocarbon is used as solvent, it is recommended, in connection with the stability and solubility of the catalyst/co-catalyst complex, that the reaction be carried out below 5° C., particularly below 0° C.

The manner in which the reactants are mixed with each other and with the catalyst and, if present, the co-catalyst is not critical. A customary method, which can also be advantageously used here, is to add the mixture of diene and dienophile, possibly mixed with some solvent, in doses to the mixture of catalyst, possible co-catalyst and solvent, while the reaction mixture is kept at the desired temperature. It is recommended that the reactions be carried out in the absence of water and oxygen.

The following examples illustrate how to perform the process according to the invention. However, the invention is not limited thereto.

EXAMPLE I

6-Phenyl-4-methyl-5,6-dihydro-2H-pyran

A mixture of 12.7 g (0.12 mol) benzaldehyde and 16.3 g (0.24 mol) isoprene in 80 ml cyclohexane was heated to 60° C. With constant and thorough stirring, 6.2 g stannic tetrachloride was added to this mixture in 30 minutes, resulting in the formation of a white precipitate. The mixture was stirred for a further 8 hours at 60° C. and subsequently, after cooling, poured out into ice water. The layers were separated, the water layer was washed with some cyclohexane and the collected organic layers with a solution of sodium bicarbonate and with a saturated solution of kitchen salt. The solvent was evaporated off and the residue distilled under reduced pressure. The desired dihydropyran was obtained in a yield of 4.7 g; boiling point 87° C. / 80 Pa; NMR (100 MHz, solution in $CCl_4$, delta in ppm relative to TMS); 1.70 (3H, broad s); 1.8–2.4 (2H); 4.20 (2H,m); 4.40 (1H, d.d.); 5.41 (1H, broad s); 7.24 (5H).

EXAMPLE II

6-Phenyl-4-methyl-5,6-dihydro-2H-pyran 12.7 g benzaldyde was dosed to a mixture of 1.4 g (0.01 mol) aluminium chloride in 100 ml cyclohexane, heated to 65° C. Subsequently 16.3 g isoprene was added in 30 minutes, followed by a further 1.4 g of aluminium chloride. The mixture was stirred a further 30 minutes at 65° C. and thereafter processed as indicated in Example I. The desired dihydropyran was obtained in a yield of 4.9 g.

EXAMPLE III

6-Phenyl-4-methyl-5,6-dihydro-2H-pyran

With thorough stirring, 3.8 g benzaldehyde was added in 5 minutes to a mixture of 6.4 g aluminium chloride and 60 g toluene, cooled to about 5° C. Subsequently, in 30 minutes, a mixture consisting of 8.9 g benzaldehyde, 17.6 g isoprene and 25 g toluene was added, with continuous cooling and thorough stirring. The mixture was stirred for a further 10 minutes at 15° C. and then processed as indicated in Example I. The desired dihydropyran was obtained in a yield of 10.1 g.

EXAMPLE IV

6-Phenyl-4-methyl-5,6-dihydro-2H-pyran

A mixture of 400 ml n-hexane and 53.3 g (0.40 mol) aluminium chloride was cooled to −5° C. while being stirred, whereafter 35.6 g (0.40 mol) 2-nitropropane was added at this temperature in 10 minutes. Subsequently, in 30 minutes, a mixture consisting of 106 g (1.9 mol) benzaldehyde, 149 g (2.2 mol) isoprene and 300 ml n-hexane was added. As the reaction is very exothermic, the mixture was continuously cooled and stirred well. The reaction mixture was subsequently stirred a further 10 minutes at −5° C., then poured into ice water and processed as described in Example I. The desired dihydropyran was obtained in a yield of 93.8 g.

EXAMPLE V

2,4-Dimethyl-6-phenyl-5,6-dihydro-2H-pyran

A mixture of 40 ml toluene and 3.2 g (0.024 mol) aluminium chloride was cooled to 5° C. while being stirred, whereafter 2.1 g (0.024 mol) 2-nitropropane was added at this temperature in 5 minutes. Subsequently, in 20 minutes, a mixture consisting of 12.7 g benzaldehyde, 23 g (0.28 mol) 2-methyl-1,3-pentadiene and 50 ml toluene was added, the mixture being continuously well stirred and cooled. The reaction mixture was stirred a further 10 minutes at 5° C., subsequently poured into ice water and processed as described in Example I. The desired dihydropyran was obtained as a mixture of 12.4 g cis-isomer and 2.0 g trans-isomer. The two isomers were separated by column chromatography over silica gel with ether/pentane as eluant.

Cis-isomer: boiling point 90° C. / 90 Pa; NMR: 1.24 (3H,d.J=7Hz); 1.70 (3H, broad s); 1.8–2.4 (2H); 4.25 (1H,m); 4.47 (1H,d.d); 5,32 (1H, broad s); 7.2 (5H).

Trans-isomer: boiling point 92° C. / 90 Pa; NMR: 1.23 (3H,d.J=7Hz); 1.72 (3H, broad s); 1.8–2.4 (2H); 4.32 (1H,m); 4.63 (1H,d.d); 5.37 (1H, broad s); 7.2 (5H).

EXAMPLE VI

4-Methyl-6-(3'-methylphenyl)-5,6-dihydro-2H-pyran

A mixture of 240 ml toluene and 10.7 g (0.08 mol) aluminium chloride was cooled to 5° C. while being stirred, whereafter at this temperature in 10 minutes 7.1 g (0.08 mol) 2-nitropropane was added, followed by 7.3 g (0.06 mol) m-tolualdehyde. Subsequently, in 1 hour, a mixture consisting of 89.5 g (0.75 mol) m-tolualdehyde and 121.2 g (1.78 mol) isoprene was added, the mixture being continuously well stirred and cooled. The reaction mixture was stirred a further 10 minutes at 5° C., subsequently poured into ice water and processed as described in Example I. The desired dihydropyran was obtained in a yield of 60.7 g; boiling point 93° C. / 80 Pa; NMR: 1.71 (3H, broad s); 1.8–2.4 (2H); 2.32 (3H,s); 4.20 (2H,m); 4.38 (1H,d.d); 5.41 (1H, broad s); 6.9–7.2 (4H).

EXAMPLE VII

4-Methyl-6-(2'-methylpropyl-1')-5,6-dihydro-2H-pyran

A mixture of 45 ml toluene and 4.4 g (0.032 mol) aluminium chloride was cooled to 5° C. while being stirred, whereafter at this temperature in 5 minutes 2.0 g (0.032 mol) nitromethane was added. Subsequently, in 20 minutes a mixture consisting of 14.0 g (0.16 mol) isovaleraldehyde, 24.0 g (0.35 mol) isoprene and 30 ml toluene was added, the mixture being continuously well stirred and cooled. The reaction mixture was stirred a further 20 minutes at 5° C., subsequently poured into ice water and processed as described in Example I. The desired dihydropyran was obtained in a yield of 5.9 g; boiling point 30° C. / 80 Pa; NMR: 0.89 (3H,d.J =7Hz); 0.91 (3H,d,J=7Hz); 0.9–2.1 (5H); 1.66 (3H,s); 3.40 (1H,m); 4.00 (2H,m); 5.32 (1H, broad s).

EXAMPLE VIII

6-Hexyl-4-methyl-5,6-dihydro-2H-pyran

A mixture of 40 ml toluene and 3.2 g (0.024 mol) aluminium chloride was cooled to 5° C. while being stirred, whereafter, at this temperature, in 5 minutes, 2.1 g (0.024 mol) 2-nitropropane was added. Subsequently, in 20 minutes a mixture consisting of 13.4 g (0.12 mol) heptanal, 20.4 g (0.30 mol) isoprene and 30 ml toluene was added, the mixture being continuously well stirred and cooled. The reaction mixture was stirred a further 20 minutes at 5° C., subsequently poured into ice water and processed as described in Example I. The desired dihydropyran was obtained in a yield of 5.4 g; boiling point 68° C. / 90 Pa; NMR: 0.89 (3H,t); 1.0–1.5 (10H); 1.66 (3H, broad s); 1.5–2.1 (2H); 3.32 (1H,m); 4.00 (2H,m); 5.32 (1H, broad s).

We claim:

1. Process for the preparation of 5,6-dihydro-2H-pyran derivatives, characterized in that an aldehyde having the formula I:

(I)

wherein $R_1$ represent an alkyl, aralkyl, alkaryl or aryl group having at most 12 carbon atoms and a diene having the formula II:

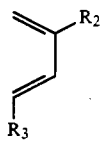
(II)

wherein $R_2$ and $R_3$ represent a hydrogen atom or an alkyl group having 1-6 carbon atoms, are converted, under the influence of inorganic Lewis acid catalyst chosen from $AlCl_3$ or $SnCl_4$, and an aliphatic or aromatic nitro compound as co-catalyst, into a compound having the formula III:

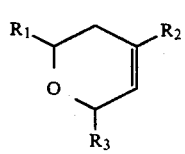
(III)

wherein $R_1$, $R_2$ and $R_3$ have the meaning indicated above.

2. Process for the preparation of 5,6-dihydro-2H-pyran derivatives, wherein an aldehyde having the formula $R_1CHO$, wherein $R_1$ represents an alkyl group having 1-6 carbon atoms, and a diene chosen from isoprene and 2-methyl-1,3-pentadiene are converted under the influence of a Lewis acid chosen from $AlCl_3$ and $SnCl_4$, in an amount of at least 0.01 mol per mol of aldehyde, into a compound having the formula:

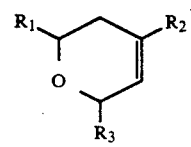

wherein $R_1$ has the meaning given above and either $R_2$ is methyl and $R_3$ is hydrogen or both $R_2$ and $R_3$ are methyl, and wherein an aliphatic or aromatic nitro compound is used as co-catalyst.

3. Process according to claim 1, characterized in that no more than 10 mol of aliphatic or aromatic nitro compound as co-catalyst is present per mol of Lewis acid chosen from $AlCl_3$ or $SnCl_4$.

4. Process according to claim 2, wherein no more than 10 mol of aliphatic or aromatic nitro compound as co-catalyst is present per mol of Lewis acid chosen from $AlCl_3$ or $SnCl_4$.

* * * * *